United States Patent [19]

Hirschfeld

[11] Patent Number: 4,654,532

[45] Date of Patent: Mar. 31, 1987

[54] APPARATUS FOR IMPROVING THE NUMERICAL APERTURE AT THE INPUT OF A FIBER OPTICS DEVICE

[75] Inventor: Tomas B. Hirschfeld, Livermore, Calif.

[73] Assignee: Ord, Inc., Nahant, Mass.

[21] Appl. No.: 773,937

[22] Filed: Sep. 9, 1985

[51] Int. Cl.⁴ .......................... G01N 21/64; G02B 6/24
[52] U.S. Cl. ............... 250/458.1; 250/461.2; 350/96.15; 436/527
[58] Field of Search ............. 250/461.2, 461.1, 458.1; 436/527, 807, 805; 422/57; 350/96.15

[56] References Cited

U.S. PATENT DOCUMENTS

| | | | |
|---|---|---|---|
| 3,779,628 | 12/1973 | Kapron et al. | 350/96.15 |
| 4,050,895 | 9/1977 | Hardy et al. | 436/527 |
| 4,133,639 | 1/1979 | Harte | 436/518 |
| 4,167,746 | 9/1979 | Storm | 357/30 |
| 4,321,057 | 3/1982 | Buckles | 356/455 X |
| 4,399,099 | 8/1983 | Buckles | 422/58 |
| 4,447,546 | 5/1984 | Hirschfeld | 436/527 |
| 4,521,070 | 6/1985 | Sottini et al. | 350/96.15 |

Primary Examiner—Janice A. Howell
Assistant Examiner—Constantine Hannaher
Attorney, Agent, or Firm—Schiller, Pandiscio & Kusmer

[57] ABSTRACT

An optical wave guide particularly useful in assay apparatus employing total internal reflection of excitation radiation at the interface between the wave guide and a surrounding liquid phase of lower index of refraction. The wave guide in the form of a solid, light-transmissive, elongated rod or fiber made typically of glass, crystal or plastic and having preferably a circular cross-section, is tapered gradually from an entrance face of relatively large diameter to a substantially smaller diameter at some position longitudinally displaced from the entrance face. In one form, the wave guide is formed with a tapering conical input portion coupled to a second portion having a cylindrical configuration and a diameter matched to the smaller diameter of the tapered portion.

16 Claims, 6 Drawing Figures

APPARATUS FOR IMPROVING THE NUMERICAL APERTURE AT THE INPUT OF A FIBER OPTICS DEVICE

This invention relates to optical apparatus for providing a transition between optical numerical apertures while conserving throughput, and more particularly to improved optical apparatus for carrying out chemical and biochemical assays.

Of the large variety of chemical and biochemical techniques used for analysis or assay, a particularly useful and sensitive one is an optical system employing the principles of attenuated total internal reflection (ATR) spectroscopy. Particularly useful for immunoassays, such an optical system employs a fiber optic wave guide, on a portion of the outer surface of which can be covalently immobilized an antibody reactive with an antigen in a test solution. A light beam introduced into one end of the wave guide will be totally internally reflected in the dense medium of the wave guide, and will generate an electromagnetic wave form, known as the evanescent wave component. The latter characteristically extends only a fraction of a wavelength across the interface between the wave guide and test solution. This penetration, however, is sufficient to permit substantial optical interaction between the evanescent wave component and the immobilized antibody with which the antigen in the test solution will complex, and only minimally with any bulk solution in which the antigen was present. Such optical interaction then permits one to assay the antigen. A number of such systems using internal total reflection spectroscopy for an assay are known and have been described, for example, in U.S. Pat. No. 4,133,639 in which is disclosed a system that measures fluorescence induced by the optical interaction; U.S. Pat. No. 4,050,895 which decribes a system based on absorption of the evanescent wave by the analyte; and U.S. Pat. Nos. 4,321,057 and 4,399,099 both of which disclose systems that detect changes in the radiation transmitted through the fiber; U.S. Pat. No. 4,447,546 which describes a fluorescence immunoassay system; and others.

A number of factors determine the sensitivity of such systems, one of the most important factors being that the sensitivity increases rapidly with the numerical aperture (NA) of the fiber at the point of contact with the surrounding medium being assayed. The sensitivity is a function with an 8th power dependence on NA at low values of the latter, and at a lower but still significant power at high values of NA.

Numerical aperture (NA) can be defined as:

(1) $NA = n_2 \sin B$ where $n_2$ is the refractive index of the medium (typically air) through which the radiation is initially propagated so as to be incident upon an input end of the fiber, and B is the maximum acceptance angle of radiation at the input end of that fiber. Thus equation (1) defines the numerical aperture at the fiber input.

Numerical aperture can also be defined as:

(2) $NA = (n_0^2 - n_1^2)^{\frac{1}{2}}$ where $n_0$ is the refractive index of the fiber core, and $n_1$ is the refractive index of the medium around the fiber (e.g. essentially the sample or bulk solution in which the antigen is disposed). Equation (2) thus may be used to define the numerical aperture at the point of contact between the fiber and the fluid being assayed. For such fiber, the numerical aperture where the surrounding medium contacts the fiber is highest when the fiber core material has a very high index and the medium surrounding it has a very low index, or $n_0 >> n_1$. For example, satisfactory sensitivities can be obtained where a glass fiber of ordinary index of refraction is surrounded by an aqueous solution that typically has an index of refraction in the vicinity of 1.33–1.35.

If the numerical aperture at the input of the fiber is less than that at the point of contact with the surrounding solution, then advantage is not being taken of the larger NA at the point of contact, and the system will not be nearly as sensitive as it could be, considering the eighth power dependence of the latter. Should the NA at the input be greater than that at the point of contact with the fiber, input radiation will spill out of the fiber at the interface and may vastly and undesirably increase background fluorescence.

While it is important to provide mounting means for the fiber so that at least that end of the fiber into which radiation is projected will be accurately positioned, contact between the fiber and the mounting will tend to reduce the numerical aperture inasamuch as the refractive index of the mounting material is generally higher than $n_1$. To reduce this problem, it has been customary to clad the fiber, at least near the end of the fiber into which radiation is propagated, with a coating, typically of a high molecular weight polymer, disposed to provide an interposed, low-refractive index medium between the mounting and the fiber. Such coating may also be opaque and exhibit preferably low reflectivity. The portion of the fiber intended to contact the analyte solution or sample to be assayed is left uncoated. Ideally, any radiation that can go through the fiber can be usefully employed if the index of the cladding is the same as the index of the sample. Unfortunately, the refractive index of most cladding obtainable is around 1.40 to 1.43, and such indices limit the maximum numerical aperture to a value much lower than the one that might be obtained if a lower index cladding were available.

Additionally, the numerical aperture can be improved by providing a clad fiber with a higher index glass core, but very high refractive index glasses are not currently commercially available as fibers with plastic, strippable cladding of low refractive index. Improvement in numerical aperture also can be achieved by insuring that radiation flux is as high as possible over the maximum solid acceptance angle of the system, and precisely mounting the clad end of the fiber becomes particularly important when the off-axis angle of incoming radiation is very large. This mounting requirement is particularly difficult to meet with respect to the very small diameter (e.g. ca. <350 microns) telecommunication fibers presently available. For example, in U.S. Pat. No. 4,050,895, there is shown the use of a number of hemispherical lenses and an annular aperture to couple large angle rays into a fiber. However, to obtain very high numerical apertures in this manner requires highly corrected lenses with shallow depth-of-field. Such lenses are difficult to fabricate, quite expensive, difficult to keep aligned, and have reduced transmission because of their typically multi-element structure. Immersion systems must currently be used for high numerical aperture illumination, but tend to be unwieldy and are also expensive.

A principal object of the present invention is therefor to provide an improved optical system which minimizes the need for immersion optics, improves the optical transmission of the fiber, permits the illuminating lenses with larger depth of focus, all with the benefit of an improved numerical aperture. Other important objects of the present invention are to provide a novel optical fiber with a substantially increased numerical aperture; and to provide such an optical fiber for total internal reflective transmission, which fiber permits the use of cladding material of ordinary refractive index to be used adjacent the portion where the fiber is mounted or held.

Yet other important objects of the present invention are to provide an improved optical system for detecting analytes at a solid-liquid interface with ATR techniques; to provide such an optical system using fiber optics with improved numerical aperture and thus an increased sensitivity; to provide such a system in which the numerical aperture achieved may be substantially as high as is allowed by the refractive indices of the sample and the fiber; to provide such a system in which the effect on the system response due to varying the refractive index of the analyte sample is reduced; to provide such a system which permits one to employ fibers of larger diameter than could heretofore be reasonably employed, and therefore make it easier to mount and align the fiber and to provide a more rugged system; to provide such a system in which the entrance area is substantially increased, thereby allowing greater light collection but in which the fiber diameter at the sampling region is reduced thereby providing greater sensitivity; to provide such a system in which the tolerance requirements for both transverse and axial alignment of the fiber are reduced; and to provide a method of improving the numerical aperture in a fiber-optic assay system.

These and other objects are realized by employing, for purposes of the present invention, a fiber tapered gradually from a relatively large diameter entrance pupil to a substantially smaller diameter at a position longitudinally displaced from the entrance pupil. Such a tapered fiber will exhibit conservation of throughput because there will be a gradual increase in the incidence angle of the radiation as the latter travels down the fiber from the entrance pupil toward the smaller diameter portion section, the numerical aperture of the radiation in the smaller cross-sectional portions becoming higher by the inverse ratio of the diameters. In other words, the light beam traversing the fiber is angularly compressed by the taper of the medium in which it is confined; the ratio of the diameters of the large and small portions of the tapered fiber is the exact inverse of the ratio of numerical apertures.

Other objects of the present invention will in part be obvious and will in part appear hereinafter.

The invention accordingly comprises the apparatus possessing the construction, combination of elements and arrangement of parts, and the method comprising the several steps and relation and order of one or more of such steps with respect to the others, all of which are exemplified in the following detailed disclosure, and the scope of the application of which will be indicated in the claims.

For a fuller understanding of the nature and objects of the present invention, reference should be had to the following detailed description taken in connection with the accompanying drawing wherein FIG. 1 shows, in idealized, enlarged cross-section, a fiber incorporating the principles of the present invention;

Figure 1:
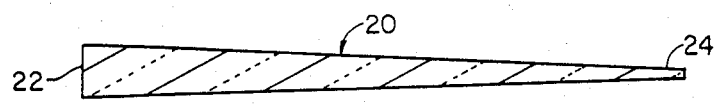

Referrring to FIG. 1, there is shown an embodiment of the present invention exemplified by fiber 20. The latter is an elongated body extending from one end or entrance face 22 to an opposite or terminal end 24, fiber 20 preferably having a substantially circular cross-section. At face 22 the fiber surface typically is planar, is disposed normally to the longitudinal axis of the fiber and is preferably highly polished to minimize any blemishes or surface defects that would tend to scatter incident excitation radiation. Alternatively, face 22 of the fiber may be configured in other desired optical shapes to serve, for example as a magnifying or matching optical surface. Fiber 20 is adapted to propagate along its length, by multiple total internal relection, optical excitation radiation entering entrance face 22 within a conical acceptance angle (B) substantially symmetric with the long axis of the fiber and defined hereinbefore, as well known to those skilled in the fiber optics art, in equation (1). Fiber 20 may be any of a very large number of substantially homogeneously materials optically transparent to the excitation radiation, e.g. glassy materials such as glass, crystalline materials such as quartz, sapphire and the like; synthetic polymers such as polyolefins, polypropylenes and the like. Where fiber 20 is to be used in fluid assays as described hereinafter, the index of refraction ($n_1$) of the material forming fiber 20 must be greater than $n_2$, the index of refration of the fluid being assayed. The latter index is typically aboout 1.3 for an aqueous solution.

In one form, fiber 20 is shaped to provide a preferably gradual, smooth, longitudinal taper from entrance face 22 to terminal end 24. This gradual transition serves to increase the input beam convergence gradually without exceeding the critical angle for the fiber. Ideally the taper of the fiber should not exceed 5°. Typically for a fiber of several millimeters in length, the diameter would then taper smoothly (i.e. not necessarily linearly but with substantially no discontinuities or abrupt angular changes in the taper angle) from an diameter of 1 mm at face 22 to a few hundred microns at end 24. If the diameter of the fiber at end 24 finally becomes smaller than some limiting value at which maximum numerical aperture is achieved, the radiation will spill or escape from fiber at that point.

Figure 2:
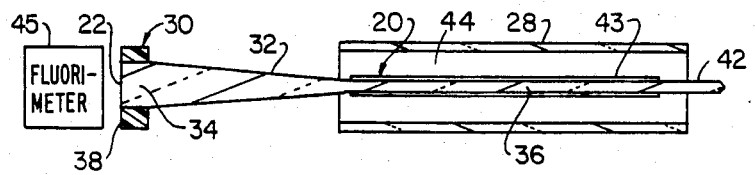
FIG. 2 illustrates, in an enlarged longitudinal cross-section, an assay device incorporating an idealized optical fiber embodying the principles of the present invention.

Referring to the embodiment shown in FIG. 2, there is shown an exemplary apparatus 26 for assaying a fluid, which apparatus incorporates the principles of the present invention. Apparatus 26 includes optical fiber 20, enclosure 28 and mounting means 30, and is similar in many respects to the system shown in U.S. Pat. No. 4,447,546 issued May 8, 1984 to one of the inventors of the present invention.

Fiber 20 of FIG. 2 has essentially the features described in connection with the embodiment of FIG. 1 except that for purposes of maximizing excitation by input radiation, tapered portion 32 thereof extends between input portion 34 and an elongated output portion 36. Both of the latter have preferably substantially constant diameters. The diameter of input portion 34 matches the larger diameter of tapered portion 32 and the diameter of output portion 36 matches the diameter of the smaller diameter of tapered portion 32. Because the surface of output portion 36 is to be used as a sampling or sensing zone for the assay, all sampling is then achieved at the highest numerical aperture of the system, i.e. at the smaller diameter end of the fiber. For purposes of an immunoassay apparatus, fiber 20 will typically be about 25 mm in length, it being understood however, that such length is merely exemplary and not limiting.

Figure 3:
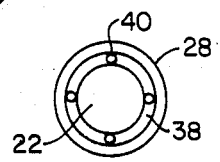
FIG. 3 is an elevational view of the input end of the assay device of FIG. 2.

Mounting means 30 is shown simply as short sleeve, cladding or ferrule 38 surrounding a short portion of fiber 20 adjacent face 22 and extending radially therefrom into contact with a portion of the internal surface of enclosure 28 adjacent one end of the latter. As shown particularly in FIG. 3, ferrule 38 is preferably provided with one or more perforations 40 extending substantially parallel to the axis of fiber 20 so as to enable fluid communication between the volumes adjacent each end of the ferrule. The primary function of ferrule 38 is to position fiber 20 so that input radiation can be directed accurately onto face 22, and also to maintain fiber 20 in spaced relation to the internal surface of enclosure 28. Because ferrule 38 necessarily is in contact with a portion of the surface of fiber 20, it may adversely affect the numerical aperture of the fiber, so it is highly desirable to limit the contact between the ferrule and fiber to a minimum commensurate with the ferrule's mechanical role, and to fabricate it of a material, such as siloxane, having a low index of refraction preferably near or matching that of the fluid to be assayed.

In an exemplary embodiment, it is intended that an operative portion such as elongated output portion 36 of the fiber surface be defined as an activated region at which the assay is to be performed. Portion 36 can be delimited by additional cladding added at opposite ends of the fiber surface so that only the desired portion of the fiber remains unclad. The dimensions of the activated region can, of course be controlled by other techniques and indeed, substantially the entire length of the fiber beyond the ferrule can constitute the activated region. However, as noted, it is desireable to configure the activated portion as a cylinder of constant diameter of the highest obtainable numerical aperture, thereby conferring the greatest sensitivity upon the system. To activate the surface of portion 36, the latter is typically coated or treated with a reagent such as those described in detail in U.S. Pat. No. 4,447,546 and incorporated herein by reference.

Enclosure 28 is a tube, preferably but not necessarily optically transparent, but formed of a material that is relatively insoluble and chemically non-reactive with the fluid being assayed. Typically enclosure 28 is simply a glass tube having an inside diameter greater than the maximum outside diameter of fiber 20, and preferably dimensioned to delimit a predetermined volume surrounding at least the activated surface of fiber portion 36.

Manufacturing of the tapered fiber can be accomplished quite simply by starting, for example, with a commercially available, constant diameter (e.g. 500 microns) glass fiber core, heating the fiber locally as with a torch or electrical heater until a local portion of the fiber becomes plastic, and then drawing the fiber at a rate and with a temperature distribution as to cause the fiber to taper to a reduced diameter, e.g. 300 microns. The minimum acceptable taper angle is governed by such practical considerations as the acceptable length of fiber, but the maximum taper angle should not exceed that necessary to preserve the necessary critical angular relationship necessary to maintain transmission by total internal reflection, and thus depends upon the index of refraction of the fiber material. For example, for a fiber core of fused quartz, the maximum taper angle should preferably be kept below about 5°. The tapered fiber may then be severed where desired. The choice of time, temperatures, drawing rates and temperature distribution of course depend largely upon the physical characteristics of the particular material chosen for the fiber. Any of a number of other known methods for drawing or forming a tapered fiber may be used. The present invention lends itself surprisingly well to formation of a double-passing fiber (i.e. one capable of transmitting light from the entrance face to the distal end and then reflecting the light back through the fiber to the entrance face if desired). Such a distal reflecting surface, located at end 42 in FIG. 2, can easily be formed simply by heating the fiber at that point and drawing the fiber at a rate high enough to rupture the fiber and form a high-angled termination which serves as a mirror capable of reflecting light in the opposite direction. Termination 42 thus can be similar in effect to a prism reflector, but can be much more simply formed without the problems attendant on formation of conventional mirrors such as grinding, plating, polishing and the like. Of course, termination 42 can simply be shaped to spill out the light, if desired, inasmuch as one can observe the fluoresence at input face 22 without interferece from the exciting radiation.

In operation of the embodiment of FIG. 2, portion 36 of fiber 20 is provided with coat 43 of any of a number of activating reagents (such as a constituent of an antibody-antigen complex that includes a fluorescent tag) and essentially subjected to the same procedure as are described in U.S. Pat. No. 4,447,546. Briefly, interspace 44 between enclosure 28 and fiber 20 is filled with a liquid sample of the material to be assayed, the sample allowed to incubate if necessary. As shown in FIG. 2, the apparatus is employed with fluorimeter 45 which provides an excitation radiation source, preferably a solid-state radiation emitter or a laser so that the wave length of the radiation can be precisely specified. Entrance face 22 is illuminated with the excitation radiation, the latter being typically capable of exciting or inducing fluorescence in the volume traversed adjacent the surface of portion 36 by an evanescent wave accompanying the transmission of the radiation down the fiber. The excitation radiation is angularly compressed from the input end of the fiber to the coated portion by the taper of the fiber, thereby increasing the numerical aperture considerably. Because the numerical aperture of portion 36 is so much greater than that of face 22, the reagent being excited by the evanescent wave is subjected to a considerably greater excitation intensity that would be experienced by an untapered fiber with the same diameter entrance face. The induced fluorescence then tunnels back into the fiber from the excited material to be read by photometer 45. Alternatively, one can position the detection portion of the photometer at the distal end of the fiber to measure the fluoresence emitted therefrom, but in such case provision should be made to discriminate between the excitation radiation and the fluoresent radiation by filtering.

For maximum sensitivity in an assay system of the present invention it is highly desirable to achieve as nearly as possible the maximum numerical aperture. As previously noted, too little loses signal as the eighth power; too large spills power out, losing some signal and increasing background fluorescence. To reproduce fibers exhibiting maximum numerical aperture requires accurate reproduction from fiber to fiber of the same ratio of the diameter of the input face to the sensitive region of the fiber, implying unrealistic manufacturing tolerances.

Figure 4:
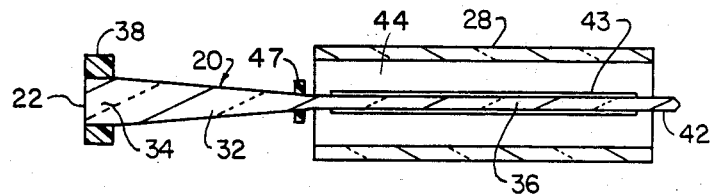
FIG. 4 illustrates, in idealized, enlarged cross-section, an alternative form of a fiber structure incorporating the principles of the present invention.

This problem can be obviated by building the fiber with an entrance diameter somewhat larger than necessary, i.e. to provide a diameter ratio $d_i/d_f$ slightly too large, $d_i$ being the diameter at the input and $d_f$ being the diameter at the final or sensitive point on the fiber. With such a structure, input radiation will start spilling out of the fiber when it reaches the sample covered portion of the fiber, the lower surrounding refractive index of air up to that point preventing energy loss through the fiber surface. This serves as a constraint on the maximum useable diameter ratio. The latter should be larger than can be accomodated by the fiber/sample interface, but smaller than that which insures total internal reflection at the fiber/air interface. This relation can be expressed as $$\sqrt{n_0^2 - n_1^2} < NA_i(d_i/d_f) < n_0 \qquad (3)$$

where $n_0$ is the refractive index of the fiber, $n_1$ the refractive index of the sample, and $NA_i$ is the numerical aperture at the input surface of the fiber. Under these conditions, the extra light collected by the larger input area will remain in the fiber until it reaches the point or zone where the surrounding medium has the same index as the sample. Because the larger $d_i$ implies larger energy input, the loss of energy will leave the net energy transfer the same as in a system of smaller $d_i$ without spilled radiation, but the spilled energy should not be permitted to create background interference. To this end, as shown in FIG. 4 (wherein like numerals denote like parts with repect to the embodiment of FIG. 2, at or adjacent the junction between portions 32 and 36, at which any radiation spilling out of the fiber will tend to cause background problems, the fiber is surrounded with radiation absorbent collar 47 in contact with the fiber around the periphery thereoof and formed of a material having an index of refraction matched to that of the sample solution as nearly as is expedient. For example, for aqueous samples, collar 47 may be a gel filled with an absorbent dye or carbon bench, or may be simply a ring of radiation absorbent plastic such as black polytetrafluoroethylene.

Not only does the increase in diameter ratios lower the manufacturing tolerance requirements, but it also serves to reduce the positioning tolerances required, both axially and transversely, for the fiber in an assay system. The increase in the area of the input face obiously decreases the transverse positioning tolerance requirement because in such case a focussed beam has more distance to wander transverely before leaving the input face. Because the increase in area also reduces the acceptance angle B required to obtain the same numerical aperture, the permissible depth of focus of the input optics is enlarged and the axial tolerance required for the input face of the fiber to remain within the depth of focus is relaxed.

The present system allows one to provide an optical fiber assay apparatus with as high a numerical aperture as may be achieved subject to the constraints imposed by the refractive index of the sample and the index of the fiber core. Since one may start with a fairly substantial glass "rod" rather than the fine fibers such as are disclosed in U.S Pat. No. 4,447,546, one is not limited to the type of glass that may be used, i.e. telecommunication glasses, and therefore one may use very high index glasses which further enhances the maximum numerical aperture that can be obtained at the fiber portion in contact with the sample. In fact, the maximum numerical aperture at the sample can now be larger than unity. To achieve this without tapering the fiber, the illuminator would have to be an immersion system. In other words, since the input numerical aperture of a tapered fiber can be lower than the numerical aperture that exists inside the tapered fiber at the point of contact with the sample, one may dispense with immersion by using a fiber which has an entrance diameter large enough so that the entrance numerical aperture stays below unity.

Further, use of the tapered fiber of the present invention permits one to use input lenses of lower numerical aperture. Such lower numerical aperture lenses are cheaper, easier to build, better corrected, tend to have higher transmission, and also have better depths of field so that focusing them is less critical.

Because the tapered fiber itself (at least at the end where it is mounted or held) may be larger in diameter than in prior art assay devices, one can use the tapered fiber to construct a system that is more rugged and has much more relaxed tolerances in positioning. And because the entrance or wide end of the taper fiber need not have a numerical aperture as large as that required by the prior art, cladding of any reasonable refractive index can be accommodated and the problem of holding or mounting the fiber is trivialized in this respect.

In assay systems using optical fibers, small uncontrollable variations in the refractive index of the sample desirably should nevertheless have a minimum effect on the readings. Small variations in the refractive index of the surface layer are also hard to control because they are dependent on the manner in which the reagent, such as an antibody layer, has been applied to the surface of the fiber. Because the tapered fibers of the present invention so improve the effective numerical aperture and one can use fibers of high refractive index in such assay devices, the importance of controlling the surface film and background refractive indices is thus much reduced and better measurements are possible. For example, in an assay device using a tapered fiber with a refractive index around 1.76, measurements made respectively using samples of water and serum showed a response variation of about 10% as contrasted with a factor of approximately 2 for a system using a standard cylindrical untapered fiber.

The advantages of the use of a tapered fiber in an fluoresence assay device are quite considerable. The limit of numerical aperture (for liquid samples) for normal fibers is roughly 0.3 if one uses extended cladding or 0.4 if only short segments of cladding are used and some loss into the cladding can be tolerated. In a tapered fiber of the present invention numerical apertures in excess of 1.0 are easily obtainable. To optimize for the particular sample being assayed, the taper ratio should be selected such that the ratio of the numerical apertures gives the wanted final numerical aperture at the sample. The maximum numerical aperture obtainable in this manner is the square root of the fiber index squared minus the sample index squared. For example, the maximum numerical aperture is 1.12 for a high index 1.76 fiber and index 1.351 sample. This high numerical aperture implies a factor of about 500 times greater sensitivity than is obtainable with standard cylindrical fibers.

The improvement in the assay apparatus signal with numerical aperture is due optimally to four factors: a square factor in the light-gathering power of the system, a square factor in the efficiency of exciting the evanescent wave, a square factor in the efficiency of collecting the fluorescence produced by the evanescent wave and a square factor in the solid angle of collection of the fluorescence. However, there is intrinsic reduction in the strengths of coupling with an increase in the index of the fiber so that at high numerical apertures, one cannot expect an 8th power enhancement. Thus, in assay apparatus with tapered fibers of high numerical aperture one only finds an improvement over the prior art by a maximum factor of roughly 500 instead of a 10,000 fold theoretical improvement. This improvement occurs partially because the thickness of the evanescent zone becomes less at high numerical aperture and therefore a smaller volume is being sampled. There is a thickness effect for the bulk sample, and where the thickness effect is absent as in a small fiber, there is a small further effect due to index mismatch and a variation in coupling strengths of radiation across the interface.

Figure 5:
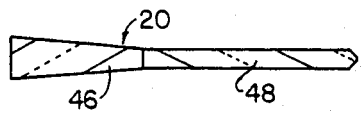
FIG. 5 illustrates, in an enlarged longitudinal cross-section an alternative assay device incorporating an optical fiber of the present invention.

In the description of the fiber of the present invention heretofore, portions 32 and 36 have been considered to be homogeneous, at least by implication, but such is not necessary and in some cases, not particularly desirable. As shown particularly in FIG. 5, fiber 20 is formed of two abutting sections, 46 and 48, corresponding respectively to portions 32 and 36, but tapered section 46 is formed of a clear, synthetic polymer such as polymethylmethacrylate, and section 48 is formed of an optical glass, due care being taken to configure the joint between the sections to provide maximum transmission of the propagated radiation along the fiber.

Figure 6:
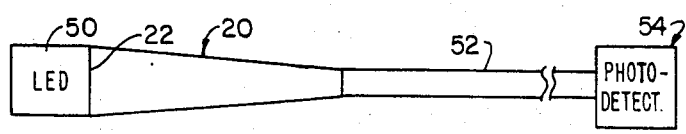
FIG. 6 shows a schematic system employing the fiber of the present invention as a transition element in a typical solid state optical transmission system.

As shown in FIG. 6, the fiber of the present invention also finds substantial utility as a transition element to match diameter of input-output optics in transmission lines. In FIG. 6, fiber 20 is coupled at input face 22 to solid-state optical source 50 such as a laser or light-emitting diode that cannot normally be reduced in size, and distal end 24 of fiber 20 is coupled to the input of transmission-quality optical fiber 52. The output of the latter in turn is connected to photoelectric sensor 54. Alternatively, if a further transition is desired, the output of fiber 52 may be connected to the smaller end of another like fiber 20, the larger end of which is then coupled to sensor 54.

Since certain changes may be made in the above apparatus and method without departing from the scope of the invention herein involved, it is intended that all matter contained in the above description or shown in the accompanying drawings shall be interpreted as illustrative and not in a limiting sense.

What is claimed is:

1. Optical apparatus comprising, in combination, a radiation source, and
an optical fiber transmissive to said radiation and comprising a first section of unclad fiber of substantially uniform cross-section diameter providing a region with a substantially constant numerical aperture, said first section being coupled to a second section of said fiber having an entrance face into which said radiation can be introduced, at least part of the periphery of said second section having cladding thereon, said second section being tapered smoothly so as to reduce the diameter thereof from said entrance face to the diameter of said first section.

2. Optical apparatus as defined in claim 1 wherein said fiber is tapered less than about 5°.

3. Optical apparatus as defined in claim 1 wherein said radiation source is a solid-state radiation emitter.

4. Optical apparatus as defined in claim 1 wherein said radiation source is a laser.

5. Optical apparatus as defined in claim 1 including detection means optically coupled to said entrance face to detect radiation travelling back down said fiber.

6. Optical apparatus as defined in claim 1 wherein the numerical aperture at said region is greater than about 1.0 when said region is surrounded by a fluid.

7. Optical apparatus as defined in claim 1 including a radiation absorbing collar disposed in contact about said fiber intermediate said entrance face and said first section.

8. In optical apparatus for performing, on a fluid sample, immunoassays with a reagent incorporating a fluorescent tag capable of emitting fluorescent radiation when excited by exciting radiation, said apparatus including an optical fiber transmissive to both said exciting radiation and said fluorescent radiation and having an entrance face into which said exciting radiation can be propagated so as to create within a zone bounded by at least a portion of the surface of said fiber in contact with said sample, an evanescent wave capable of exciting fluorescent radiation from tags that may be disposed in said zone,
the improvement wherein said fiber comprises a first section of unclad fiber of substantially uniform cross-section diameter, said zone being located in said first section so as to probide said zone with a substantially constant numerical aperture, said first section being coupled to one end of a second section of said fiber having said entrance face at the opposite end thereof, at least part of the periphary of said second section having cladding thereon, said second section being tapered smoothly so as to reduce the diameter thereof from said entrance face to the diameter of said first section.

9. Optical apparatus as defined in claim 8 wherein said reagent is an antigen-antibody complex.

10. Optical apparatus as defined in claim 8 including means for delimiting a volume including said zone and bounded, at least in part, by said portion of said fiber surface.

11. Optical apparatus as defined in claim 10 wherein said volume is of capillary dimensions.

12. Optical apparatus as defined in claim 10 wherein said means for delimiting comprises elongated enclosure means surrounding and spaced from at least said portion of said fiber surface.

13. Optical apparatus as defined in claim 8 wherein the numerical aperture of said fiber at said zone is defined as $(n_o^2-n_1^2)^{\frac{1}{2}}$, $n_o$ and $n_l$ being respectively the indices of refraction of said fiber and said sample, and wherein the numerical aperture at said entrance face is lesser than said numerical aperture at said zone, the angle of said taper being chosen to provide said numerical aperture at said zone substantially without radiation loss though the tapered surface of said fiber.

14. Optical apparatus as defined in claim 8 including a radiation absorbing collar disposed in contact about said fiber adjacent the juncture of said first and second sections, the material of said collar in contact with said fiber being selected to have an index of refraction substantially matched to the index of refraction of said sample.

15. Optical apparatus as defined in claim 8 including detection means optically coupled to said entrance face to detect radiation travelling back down said fiber.

16. Optical apparatus as defined in claim 8 wherein the numerical aperture at said zone is greater than about unity.

* * * * *